US011513129B2

(12) United States Patent
Sane et al.

(10) Patent No.: US 11,513,129 B2
(45) Date of Patent: Nov. 29, 2022

(54) DEVICE FOR QUANTITATIVE MEASUREMENT OF THYROID HORMONES

(71) Applicants: Eshan Shriniwas Sane, Westborough, MA (US); Anoop Tej Patta, Westborough, MA (US); Krish Kalyan Nathan, Westborough, MA (US)

(72) Inventors: Eshan Shriniwas Sane, Westborough, MA (US); Anoop Tej Patta, Westborough, MA (US); Krish Kalyan Nathan, Westborough, MA (US)

( * ) Notice: Subject to any disclaimer, the term of this patent is extended or adjusted under 35 U.S.C. 154(b) by 394 days.

(21) Appl. No.: 16/750,446

(22) Filed: Jan. 23, 2020

(65) Prior Publication Data
US 2020/0241017 A1 Jul. 30, 2020

Related U.S. Application Data

(60) Provisional application No. 62/797,305, filed on Jan. 27, 2019.

(51) Int. Cl.
| | | |
|---|---|---|
| *G01N 33/78* | (2006.01) | |
| *B01L 3/00* | (2006.01) | |
| *G01N 27/06* | (2006.01) | |
| *G01N 27/403* | (2006.01) | |

(52) U.S. Cl.
CPC .............. *G01N 33/78* (2013.01); *B01L 3/508* (2013.01); *G01N 27/06* (2013.01); *G01N 27/403* (2013.01); *B01L 2300/024* (2013.01); *B01L 2300/025* (2013.01); *B01L 2300/0825* (2013.01)

(58) Field of Classification Search
CPC ...... G01N 33/78; G01N 27/06; G01N 27/403; G01N 33/48707; G01N 27/3275; B01L 3/508; B01L 2300/024; B01L 2300/025; B01L 2300/0825
See application file for complete search history.

(56) References Cited

U.S. PATENT DOCUMENTS

2012/0132797 A1 5/2012 Strauss et al.

OTHER PUBLICATIONS

Goncalves et al, "Proof of Concept of the Electrochemical Sensing of 3-Iodothyronamine (T AM) and Thyronamine (T AM)" ChemElectroChem, vol. 1 Issue 10, Oct. 14, 2014, pp. 1623-1626. (Year: 2014).*
DeRuiter et al., "Thyroid hormone tutorial: the thyroid and thyroid hormones," Endocrine Pharmacotherapy Module: Thyroid Section, Summer 2002, 2001, 16 pages.
Jeon et al., "Disposable non-enzymatic glucose sensors using screen-printed nickel/carbon composites on indium tin oxide electrodes," Sensors, Dec. 2015, 15(12):31083-91.
Khan et al., "Serpin inhibition mechanism: a delicate balance between native metastable state and polymerization," Journal of Amino Acids, May 24, 2011, 11 pages.
Law et al., "An overview of the serpin superfamily," Genome Biology, May 30, 2006, 7(5):1-1, 11 pages.
LSBU [online], "Amperometric Biosensors," 2004, retrieved on Aug. 5, 2020 from URL <http://www1.lsbu.ac.uk/water/enztech/amperometric.html>.

(Continued)

*Primary Examiner* — Dennis White
(74) *Attorney, Agent, or Firm* — Fish & Richardson P.C.

(57) ABSTRACT

The present application relates to a method for detecting and monitoring the level of thyroid hormones in an individual and a device for carrying out the same.

18 Claims, 5 Drawing Sheets

(56) References Cited

OTHER PUBLICATIONS

PubChem [online], "Thiosulfate, O3S2-2," National Center for Biotechnology Information, U.S. National Library of Medicine, dated Aug. 8, 2005, retrieved from URL <https://pubchem.ncbi.nlm.nih.gov/compound/Sodium-thiosulfate>, 32 pages.

Taggart et al., "Oxidation of either methionine 351 or methionine 358 in α1-antitrypsin causes loss of anti-neutrophil elastase activity," Journal of Biological Chemistry, Sep. 1, 2000, 275(35):27258-65.

Toghill et al., "Electrochemical non-enzymatic glucose sensors: a perspective and an evaluation," International Journal of Electrochemical Science, Sep. 1, 2010, 5(9):1246-301.

Van Patten et al., "Oxidation of methionine residues in antithrombin effects on biological activity and heparin binding," Journal of Biological Chemistry, Apr. 9, 1999, 274(15):10268-76.

Yoo et al., "Glucose biosensors: an overview of use in clinical practice," Sensors, May 2010. 10(5):4558-76.

\* cited by examiner

Regression Line:

$y = 5.13 + 1.782 \cdot x$

Correlation Coefficient:

DEVICE FOR QUANTITATIVE MEASUREMENT OF THYROID HORMONES

This application claims the benefit of priority of U.S. Prov. Appl. No. 62/797,305, filed Jan. 27, 2019, which is incorporated herein by reference in its entirety.

TECHNICAL FIELD

The present application relates to a method for detecting and monitoring the level of thyroid hormones in an individual and a device for carrying out the same.

BACKGROUND

Thyroid disease is extremely prevalent as it affects twenty million Americans and hypothyroidism, the most common form, occurs when not enough thyroid hormone is produced in the body. Consequently, deficient levels of thyroid hormone lead to symptoms such as constant tiredness, hair loss, and a host of other issues related to metabolism. Although there exist thyroid hormone tests which can be accessed at the doctor's office, they are time-consuming, costly, and inconvenient to access. As a result, many individuals with hypothyroidism do not get hormone levels checked frequently enough, which causes the disease to progress and worsen. Early and frequent screening will help reduce cases of hypothyroidism. As patients with thyroid diseases must periodically get their thyroid levels checked, insurance bills get more expensive and more money is taken out of the pockets of individuals who must combat this chronic disease for the entirety of their life. Therefore, there is a need for a more economically efficient and convenient method to periodically check the thyroid hormone levels.

SUMMARY

Provided herein is a method for measuring the quantity of thyroid hormone in a sample, wherein the method comprises:

a) isolating thyroid hormones in a sample;
b) measuring the background electrical quantities of a solution of thyroid hormone isolated from step a);
c) contacting a first chemical agent to the solution of step b), wherein the first chemical agent removes one or more iodine from the thyroid hormone;
d) contacting a second chemical agent to the solution of step c), wherein the second chemical agent prevents the free iodide ions from forming $I_2$;
e) contacting a cationic agent to the solution of step d), wherein the cationic agent forms a salt with the free iodide ions; and
f) measuring the electrical quantities of voltage generation and resistance in the solution of step e).

In some implementations, the method further comprises applying a conversion factor to convert the voltage produced by the electrolyte solution to a concentration of thyroid hormone.

In some implementations, the thyroid hormone is T4. In some implementations, the T4 is bound T4 in the bloodstream.

In some implementations, the first chemical agent comprises of deiodinases, catalysts, biomolecules, and combination thereof, wherein the deiodinases, catalysts, and biomolecules are suitable for breaking iodine-carbon bond between iodine and thyroid hormone. In some implementations, the first chemical agent removes one iodide from T4. In some implementations, the first chemical agent removes two iodides from T4. In some implementations, the first chemical agent removes three iodides from T4. In some implementations, the first chemical agent removes four iodides from T4.

In some implementations, the second chemical agent comprises thiosulfate.

In some implementations, step a) of isolating thyroid hormone from a sample comprises filtering ions from the sample. In some implementations, the cationic agent comprises sodium. In some implementations, the second chemical agent and the cationic agent is sodium thiosulfate.

Provided herein is also a device for measuring the quantity of thyroid hormone in a sample, wherein the device is configured to implement one or more steps a)-f) described herein. In some implementations, the device comprises a microcontroller, and the microcontroller presents readings from the measurement to a user. In some implementations, the device comprises a testing strip coated in the reactants to receive the sample. In some implementations, the device comprises an electrochemical cell configured to conduct the measurement of the quantity of thyroid hormone in the sample. In some implementations, the electrochemical cell comprises the first chemical agent on the test strip. In some implementations, the device comprises circuitry and wires substantially as described in FIG. 3. In some implementations, the device is configured to store thyroid health data.

DETAILED DESCRIPTION

The present application relates to methods of monitoring thyroid levels and a device for carrying out these methods. The methods and devices described herein provide a quick result and update of an individual's metabolic disorders and the repercussions that derive from them. By quantifying thyroxine (T4), this would provide an appropriate analysis of the current metabolic condition of a patient with a thyroid hormone disorder. Thyroxine hormone is the most common in the bloodstream and is generated in the thyroid gland if the thyroid is functioning properly. If the thyroid gland is not functioning properly, it could mean that the pituitary gland in the brain is secreting either an excess or lack of TSH, another critical thyroid hormone (a controlling/signaling hormone), telling the thyroid gland to increase or decrease the synthesis of thyroxine beyond the correct bodily levels. This imbalance damages the thyroid gland, and leads to various endocrine problems and decreased autoimmune efficiency.

Both T4 and TSH can serve as indicators of thyroid health, as well as T3. However, out of these, T4 is a good candidate for testing and measurement. Besides T4 having a greater relative quantity, it is also more viable than TSH as T4 is transported throughout the bloodstream by various transport proteins, including TBG and Transthyretin. A test for either the T4 itself or activation of the transport proteins can provide a good measurement of thyroid health. A feature of T4 is the iodine present. The method for quantifying T4 involves finding the quantity of iodine, which is attached to the carbon atoms in a single bond. As used herein, iodine refers to (I) and iodide refers to its ionic form (I$^-$). It is important to note that there are molecules, both biological and synthetic, which break down the T4 molecule and remove the iodine from the T4 molecule, and break down or prevent formation of iodine-iodine bonds. Examples of these types of molecules are thiosulfate, which is not naturally present in the body, but is commonly used to break iodine-iodine bonds, and biomolecules such as iodothyronine deiodinase (and other deiodinase-category enzymes), which the body uses in its own breakdown of the hormone in its destination cell.

The method for quantifying iodide in solution once it has been dissociated involves measuring its electrical properties in its sample solution, such as the voltage generated by the ions. Another facet of this method relates to the filtration of confounding ions which may generate background voltage, affecting the true measurement. Commonly, methods such as ultrafiltration, separation of particles by creating a pressure difference across a semipermeable membrane, are used to combat this issue. In addition, taking a baseline measurement prior to the experiment and subtracting it from the value measured after the reaction has occurred will reduce noise in the data. The voltage generated by free iodide in a sample will increase proportionally to the amount of iodide in that sample, which can then quantify the amount of T4 which originally contained that iodide in the form of iodine (non-ionic).

Provided herein are methods for measuring the quantity of thyroid hormone in a sample, wherein the method comprises:

a) isolating thyroid hormones in a sample;

b) measuring the background electrical quantities of a solution of thyroid hormone isolated from step a);

c) contacting a first chemical agent (e.g., a dissociative agent) to the solution of step b), wherein the first chemical agent removes one or more iodide ions from the thyroid hormone;

d) contacting a second chemical agent to the solution of step c), wherein the second chemical agent prevents the free iodide ions from forming $I_2$;

e) contacting a cationic agent to the solution of step d), wherein the cationic agent forms a salt with the free iodide ions; and f) measuring the electrical quantities of voltage generation and resistance in the solution of step e).

Step a) of isolating thyroid hormone from a sample can include filtering ions from the sample. Removing ions eliminates background voltage that could affect the true measurement.

The method further comprises applying a conversion factor to convert the voltage produced by the electrolyte solution to a concentration of thyroid hormone. The thyroid hormone of interest for measurement is T4, e.g., bound T4 in the bloodstream, which represents 98% of the inactive T4.

Examples of first chemical agents (e.g., dissociative agent) include deiodinases (e.g., type 2 and 3 deiodinase, or Dio2 and Dio3), catalysts, biomolecules, and combination thereof, where the deiodinases, catalysts, and biomolecules are suitable for breaking iodine-carbon bond between iodine and thyroxine molecule. Such agents can remove one, two, three, or four iodides from T4.

An example of a second chemical agent is thiosulfate. An example of a cationic agent is sodium. Sodium thiosulfate can serve as the second chemical agent and the cationic agent.

In addition to having a new theoretical method of quantifying T4 content in the bloodstream, a device is provided which can perform this measurement in a sample, e.g., by carrying one or more steps described herein. The device is in the form of a module with a testing strip to capture a patient's sample and an electrochemical cell to conduct the measurement of the quantity of thyroid hormone in the sample. The electrochemical cell contains a dissociative agent to produce free iodide ions from thyroid hormone present in the patient's sample. In particular, the dissociative agent will be paired with a cation, such as sodium. The sodium cation will form a salt with the free iodide ions produced by the reaction, and the addition of thiosulfate will prevent $I_2$ bonds from forming. The change in voltage of the electrochemical cell due to the reaction between thyroid hormone and the dissociative agent, which generates free iodide ions, can be proportionally related to the concentration of thyroid hormone in the cell. Using experimental data, it is possible to make a linear regression with the concentration of thyroid hormone in the sample as the independent variable and the electricity produced by the cell as the dependent variable. Such a regression can be used to accurately predict the concentration of thyroid hormone in the patient's sample. The implementation of this in a home-based device will involve having one removable portion where the patients sample is added. This removable portion will be coated with the dissociating agent and sodium thiosulfate, which will begin the reaction process. Once this is inserted into the main device, the electrical signals will be measured by a voltage sensor, stored and processed, and converted back into a reading of thyroid hormone concentration to be displayed to the user.

The present disclosure provides a mechanism to quickly and accurately measure the concentration of T4 in a given sample. This allows patients to conveniently and frequently measure their thyroid hormone levels. These measurements will provide the patient and their healthcare provider with more granular data to diagnose and treat the patients' thyroid condition at a better level. The present invention may serve a similar role for thyroid patients as home blood glucose monitors for diabetics. A common method to measure free T4, which is frequently used at doctors' offices, is a free T4 assay. The main drawback to this test is the time and cost, as expensive laboratory equipment is needed to read the results. The present disclosure provides a mechanism to measure T4 which requires less time and is less expensive than traditional lab tests, yet still provides sufficient precision so as to be useful to the patient.

The method provide herein can further include treating a patient (e.g., a user of a device described herein) with thyroid disease. The treatment can include administering to the patient T4 hormone (e.g., synthetic T4 such as levothyroxine) for patient with hypothyroidism or radioactive iodine for patient with hyperthyroidism.

The healthy range of total T4 blood concentration in healthy adults is between 4.6 and 11.2 mcg/dL. There should be a working precision to a factor smaller and larger than this range in order to provide diagnostically significant measurements to doctors and patients. The present invention may achieve this precision in a cost-effective manner by utilizing a chemical reaction involving thyroid hormone to produce electricity, as previously detailed. In particular, the precision of the measurement can be increased by using a reference solution with constant electrochemical properties to calibrate the voltage sensor before each measurement. In addition, the chemical conditions of the reaction must be accurately replicated during each measurement. A test strip which contains the correct concentrations of the reactants may be used to capture the patients' sample and achieve consistent chemical conditions during each measurement. These test strips would be one-use and could be mass produced to lower their cost significantly. The main voltage testing unit would be a one time purchase.

A major part of helping a user understand the readings which are in the unit of voltage is converting from these output values into readings useful to the user, in terms of their thyroid hormone content and their overall thyroid health. The outputs can be converted to the thyroid hormone through a process which was tested in a set of preliminary experiments which provide further evidence that our method of quantifying thyroid hormone will be effective.

This method consists of two phases; one where test solutions were prepared with L-tyrosine and iodine. L-tyrosine is the molecular equivalent of the broken down thyroxine (T4) with the iodine's removed, which were also present in the solution as iodine-iodine ($I_2$) molecules. Given this, the test solution used was a good indicator of a human sample once the T4 molecules were dissociated by a mixture of deiodinase enzymes (type 2 and 3 deiodinase, or Dio2 and Dio3) and thiosulfate. The second phase of this method involves adding a cation, specifically sodium, to this sample solution, and measuring the output voltage. Thiosulfate was also added at this step to prevent free iodide ions from bonding with one another. The voltage output was measured using this method at five different L-tyrosine+iodide concentrations, and a correlation was determined between the increase in voltage measured and the additional iodine content added. This was also compared against baseline measurements, which were taken by removing only one of the reactants from the solution each time ("removed" by re-creating the solution without the given reactant) and taking the voltage output measurements. The baseline measurements were consistently lower than the measurements with all the reactants, indicating that the iodide ion concentration can be determined best by using a solution with a cation (sodium in our case) and thiosulfate by measuring its electrical output.

Figure 1:
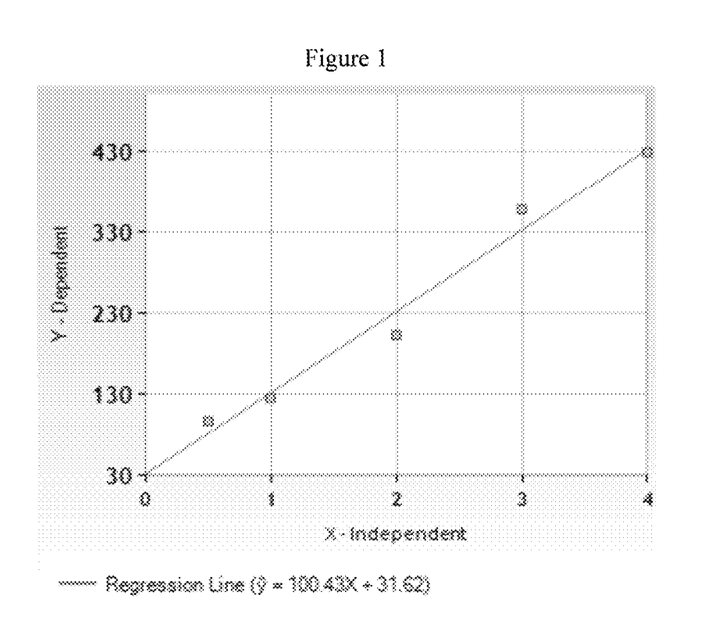
FIG. 1 is a graph showing the values from Table 1. The concentration is on the x axis (converted back to mL of solution added, a 37.5 µg/mL ratio) and the mV measured is on the y axis.
Figure 2:
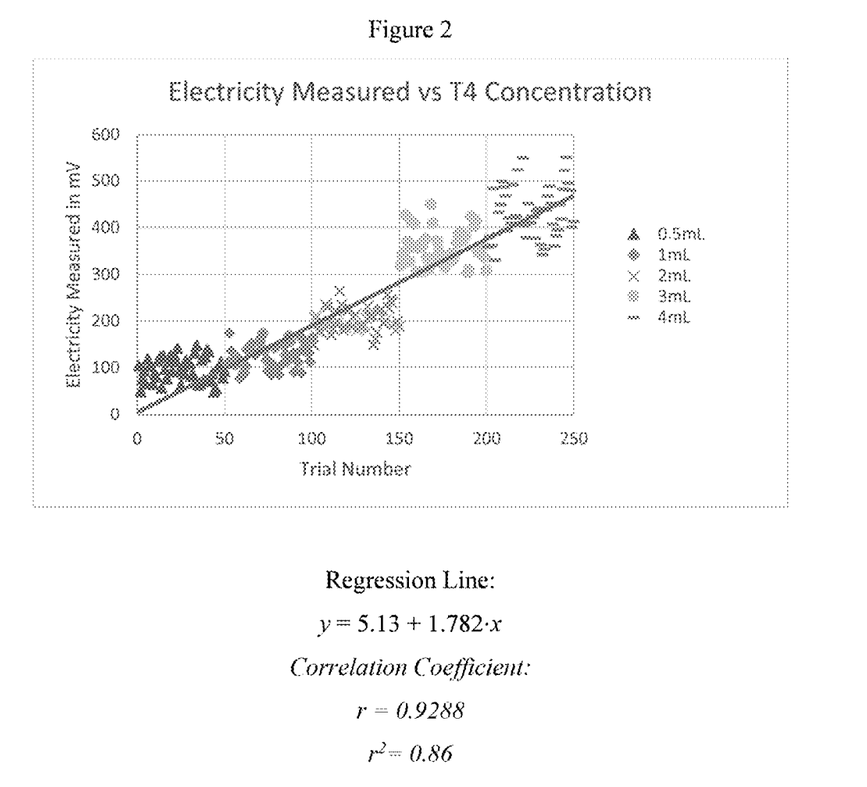
FIG. 2 is a graph showing the total set of 250 data points taken for electricity measured and T4 concentration, which are divided into 5 groups at concentrations given in the key.

In the case of voltage, the values in Table 1 (plotted in FIG. 1) are averages from the total set of 50 trials at 5 concentrations. The averages at each concentration were plotted on a line of best fit, where the dependent variable was the output voltage. The concentration is on the x axis (converted back to mL of solution added, a 37.5 µg/mL ratio) and the mV measured is on the y axis. The line of best fit for this data was linear, following an equation of $y=100.427073x+31.619146$, where y was voltage in mV and x was the concentration of the L-tyrosine+iodide added, in µg increments of 37.5 µg corresponding to each increase in x of 1. This had a correlation coefficient of 0.9893, which is likely due to each average being taken from 50 trials. This provides strong evidence that the increasing iodide concentrations contributed to the increased electrolyte concentrations in the solution and therefore this method can be used to quantify the free iodide in a given sample to the microgram scale, our goal being a human sample once it is filtered for thyroxine and iodine is unbound from the thyroxine molecule and becomes iodide (ionic form). Schemes 1 and 2 show the proposed method of deiodinating thyroxine and maintaining free iodide in the sample using deiodinase and thiosulfate. FIG. 2 is a graph showing the total set of 250 data points taken, which are divided into 5 groups at concentrations given in the key. A regression line is drawn through all the data, which has a correlation described to the right. The key feature in this graph is the upward trend for the averages of each concentration, which is what FIG. 1 demonstrates. Concentration of test solution in mL represents 37.5 µg of iodide and excess L-tyrosine per mL (0.5 mL sample would have half of this iodide value, for example). In the appendix attached, the individual data values, the histogram distributions, and the baseline measurements for each concentration are provided.

TABLE 1

| L-tyrosine + Iodide (Broken-down T4) content, with iodide as the limiting reactant listed | Average voltage measured |
| --- | --- |
| 18.75 µg | 96.96 mV |
| 37.5 µg | 126.42 mV |
| 75 µg | 202.18 mV |
| 112.5 µg | 357.42 mV |
| 150 µg | 429.60 mV |

Table 1 shows the average voltages of all 50 trials at each concentration tested. Clear proportional relationship demonstrated here, with line of best fit graph shown in FIG. 1.

Scheme 1 shows the pathway that the deiodinase enzyme dissociates the iodine incrementally from the T4 hormone. After the two deiodinase reactions are carried out, two out of four iodine will be free from the hormone to create a solution with an ionic character once paired with a cation.

Scheme 1

Thyroxine (T₄)      Triiodothyronine (T₃)

Type III Deiodinase (Dio3)      Type III Deiodinase (Dio3)

Reverse T$_3$ (rT$_3$)

Diiodothyronine (T$_2$)

Scheme 2 shows the reaction between iodine and thiosulfate which dissociates any iodine bonds which form from the free iodide ions, maintaining that the solution has free iodide ions once it has been dissociated from the thyroid hormones. Scheme 2. Reaction between iodine and thiosulfate to create iodide and tetra-thionate.

$$I_2 + 2S_2O_3^{2-} \rightarrow 2I^- + S_4O_6^{2-}$$

Iodine+thiosulphate→iodide+tetra-thionate

As described earlier, this method can be implemented into a device. The device involves quantifying thyroid hormone and applying this method to a small, home based system that can perform these electrochemical reactions on a patient's blood sample and provide a reading of thyroid hormone concentration. A finger-prick mechanism akin to blood glucose meters will be used to add a drop of blood to a removable test strip, which will be inserted into the main unit to be measured, stored, and displayed. The goal is for patients to be able to obtain a measurement of their thyroid hormone content fluctuating at a weekly basis rather than monthly (which is the current testing time). This will lead to better medication prescription and better understanding of the patient's thyroid condition over time.

Figure 3:
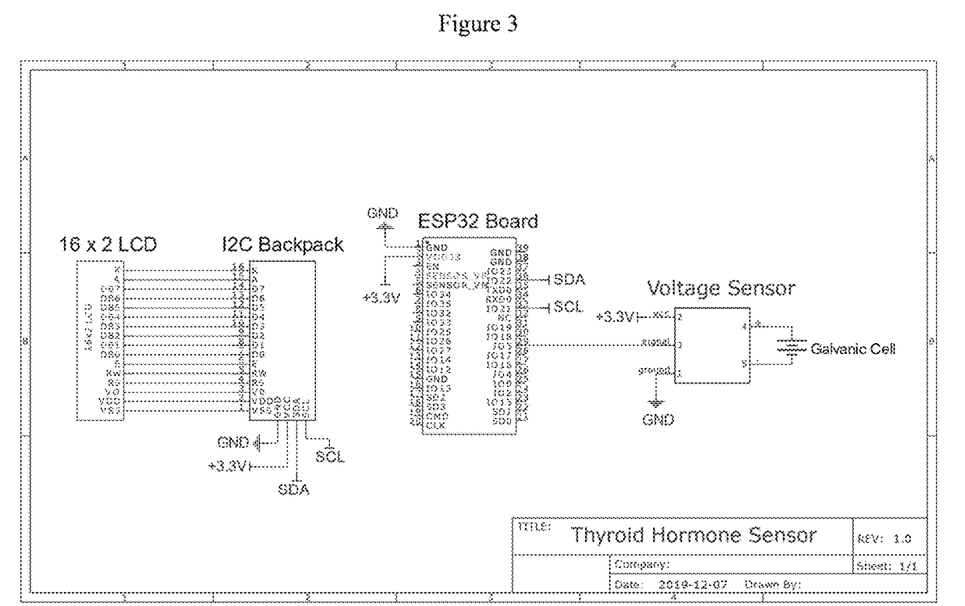
FIG. 3 is a schematic diagram showing the circuitry and wires between the inputs connecting the voltmeter, a microcontroller, and the LCD display.

FIG. 3 shows the circuitry and wires between the inputs connecting the voltmeter, a microcontroller, and the LCD display. This figure represents the prototype implementation of an exemplary device described herein. Specifically, this is the main unit to which the test strips/trays would be inserted for voltage measurement. The voltmeter is configured to a measuring tray containing the electrochemical cell with the patient's sample and the reactants. A prototype engineered such that the patient could slide in their sample and the device would automatically turn on and begin analyzing their sample would be easiest for the patient. The current scale of this design is 6 inches vertically by 8 inches across, but this could be changed or decreased by shrinking the size of the microcontroller, as an arduino processor was used for testing, which is much bigger than other microcontrollers. The test strips would be 2×3 inches, and would attach to the voltmeter prongs in the main unit.

Figure 4:
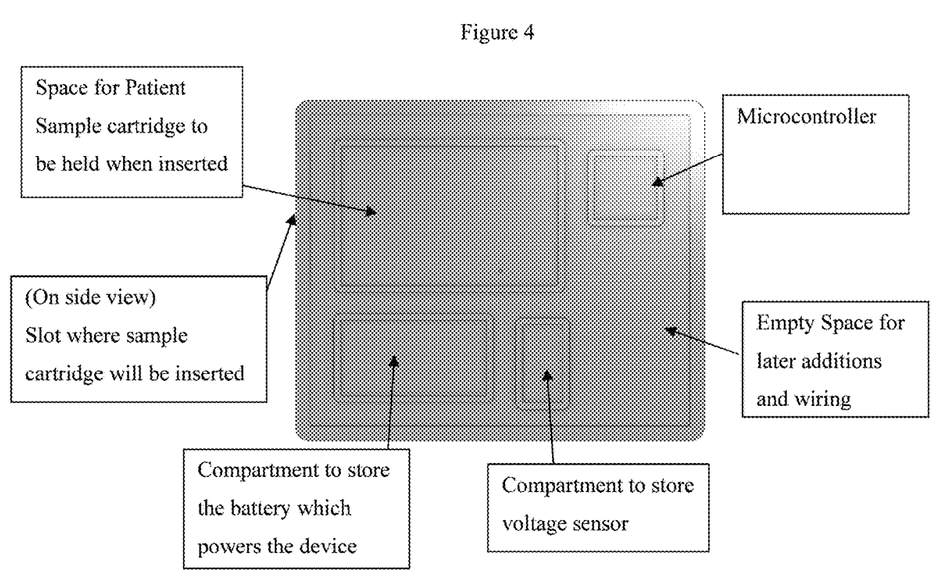
FIG. 4 is an exemplary representation showing a top view of the compartment which houses the components of the device.

FIG. 4 is an exemplary representation showing a top view of an exemplary compartment which houses the components of the device. The top right compartment houses the microcontroller, which processes data from the voltage sensor to generate hormone measurements and transmits data to a mobile app. The top left compartment houses the cartridge for the patient's sample, which slides into the device through a side cutout. The bottom center compartment houses the voltage sensor, which connects to the cartridge containing the patient's sample and measures the previously described reaction. The bottom left compartment houses the battery which powers the device. On top of this is a lid in which there's an embedded LCD screen displaying the voltage reading from the microcontroller which will be wired to it. These wires will have enough slack to be able to open the lid to replace the battery without damaging the microcontroller to LCD connection.

Figure 5:
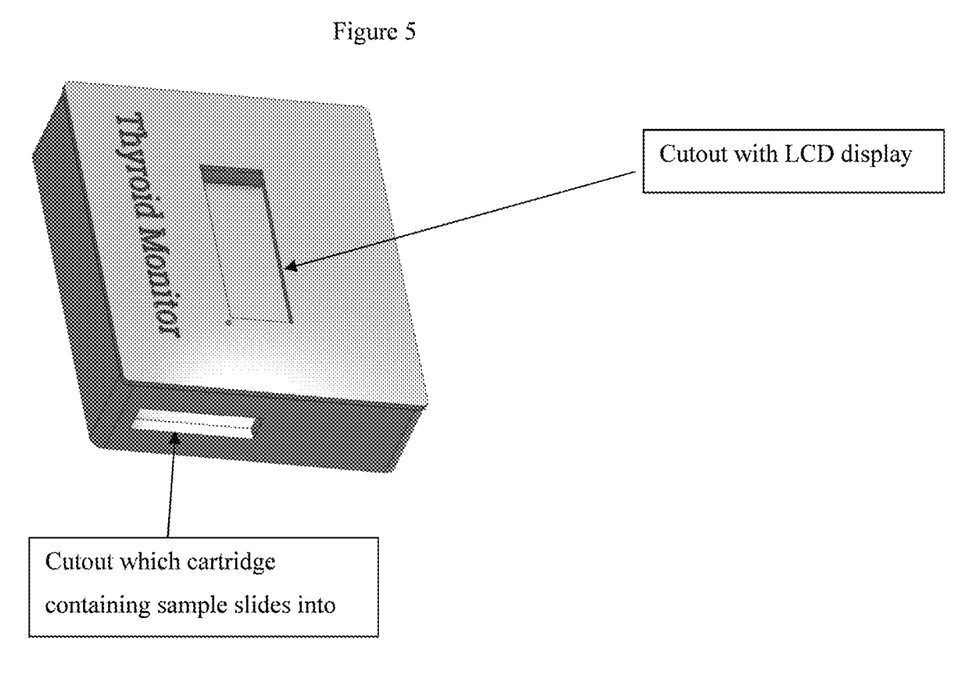
FIG. 5 is an exemplary representation showing a corner view of the device.

FIG. 5 is an exemplary representation showing a corner view of an exemplary device. The cutout shown allows a cartridge containing a sample to slide into the device. Once it is inserted, it will connect to the voltmeter, which will have metal prongs that reach into the compartment where the sample will be inserted on a removable cartridge. This will connect to the cartridge and take the electrical measurements once it is fully inserted. It will then display these on the LCD via the microcontroller as described in FIG. 3. The LCD on top of the closed lid is also shown.

All publications, patent applications, patents, and other references mentioned herein are incorporated by reference in their entirety. Unless otherwise defined, all technical and scientific terms used herein have the same meaning as commonly understood by one of ordinary skill in the art to which this invention belongs. In case of conflict, the present specification, including definitions, will control. Suitable methods and materials are described below, although methods and materials similar or equivalent to those described herein can also be used in the practice or testing of the present invention. The materials, methods, and examples are illustrative only and not intended to be limiting.

What is claimed is:

1. A method for measuring the quantity of thyroid hormone in a sample, wherein the method comprises:
   a) isolating thyroid hormones in a sample;
   b) measuring the background electrical quantities of a solution of thyroid hormone isolated from step a);
   c) contacting a first chemical agent to the solution of step b), wherein the first chemical agent removes one or more iodide ions from the thyroid hormone;
   d) contacting a second chemical agent to the solution of step c), wherein the second chemical agent prevents the free iodide ions from forming I$_2$;
   e) contacting a cationic agent to the solution of step d), wherein the cationic agent forms a salt with the free iodide ions;
   f) measuring the electrical quantities of voltage generation and resistance in the solution of step e); and
   g) applying a conversion factor to convert the voltage produced by the electrolyte solution to a concentration of thyroid hormone.

2. The method of claim 1, wherein the thyroid hormone is T4.

3. The method of claim 2, wherein the T4 is bound T4 in the bloodstream.

4. The method of claim 1, wherein the first chemical agent comprises of deiodinases, catalysts, biomolecules, and combination thereof, wherein the deiodinases, catalysts, and biomolecules are suitable for breaking iodine-carbon bond between iodine and thyroid hormone.

5. The method of claim 2, wherein the first chemical agent removes one iodide from T4.

6. The method of claim 2, wherein the first chemical agent removes two iodides from T4.

7. The method of claim 2, wherein the first chemical agent removes three iodides from T4.

8. The method of claim 2, wherein the first chemical agent removes four iodides from T4.

9. The method of claim 1, wherein the second chemical agent comprises thiosulfate.

10. The method of claim 1, wherein step a) of isolating thyroid hormone from a sample comprises filtering ions from the sample.

11. The method of claim 1, wherein the cationic agent comprises sodium.

12. The method of claim 1, wherein the second chemical agent and the cationic agent is sodium thiosulfate.

13. A device for measuring the quantity of thyroid hormone in a sample, wherein the device is configured to implement steps b) to g) of claim 1, and the device comprises an electrochemical cell configured to conduct the measurement of the quantity of thyroid hormone in the sample.

14. The device of claim 13, wherein the device comprises a microcontroller, and wherein the microcontroller presents readings from the measurement to a user.

15. The device of claim 13, wherein the device comprises a testing strip coated in the reactants to receive the sample.

16. The device of claim 13, wherein the electrochemical cell comprises the first chemical agent on a test strip.

17. The device of claim 13, wherein the device comprises circuitry and wires between the inputs connecting a voltmeter, a microcontroller, and a LCD display.

18. The device of claim 13, wherein the device is configured to store thyroid health data.

* * * * *

UNITED STATES PATENT AND TRADEMARK OFFICE
CERTIFICATE OF CORRECTION

PATENT NO. : 11,513,129 B2
APPLICATION NO. : 16/750446
DATED : November 29, 2022
INVENTOR(S) : Sane et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 463 days.

Signed and Sealed this
Sixth Day of February, 2024

Katherine Kelly Vidal
*Director of the United States Patent and Trademark Office*